(12) United States Patent
Goto et al.

(10) Patent No.: US 6,734,960 B1
(45) Date of Patent: May 11, 2004

(54) WAFER DEFECT MEASURING METHOD AND APPARATUS

(75) Inventors: Hiroyuki Goto, Hadano (JP); Hiroyuki Saito, Kitakanbara-gun (JP); Makiko Fujinami, Uji (JP); Hiroshi Shirai, Hadano (JP)

(73) Assignee: Toshiba Ceramics Co., Ltd., Tokyo (JP)

( * ) Notice: Subject to any disclaimer, the term of this patent is extended or adjusted under 35 U.S.C. 154(b) by 337 days.

(21) Appl. No.: 09/589,087

(22) Filed: Jun. 8, 2000

(30) Foreign Application Priority Data

| Jun. 9, 1999 | (JP) | ................................. 11-162570 |
| Aug. 12, 1999 | (JP) | ................................. 11-228534 |
| Oct. 29, 1999 | (JP) | ................................. 11-309106 |
| Feb. 4, 2000 | (JP) | ................................. 2000-027770 |
| Jun. 5, 2000 | (JP) | ................................. 2000-167540 |

(51) Int. Cl.⁷ .............................................. G01N 21/00
(52) U.S. Cl. .................................................. 356/237.1
(58) Field of Search ........................... 356/237.1, 237.3, 356/237.4, 237.5, 446; 250/559.41, 559.45, 559.43, 559.4, 492.2; 348/125, 126; 382/145, 147, 149; 374/45, 46, 47, 161

(56) References Cited

U.S. PATENT DOCUMENTS

| 4,211,488 A | * | 7/1980 | Kleinknecht | ............ | 250/559.16 |
| 5,196,716 A | * | 3/1993 | Moriya et al. | ............ | 250/559.16 |
| 5,881,208 A | * | 3/1999 | Geyling et al. | ............ | 392/418 |
| 5,894,345 A | * | 4/1999 | Takamoto et al. | ........ | 356/237.1 |
| 6,157,444 A | * | 12/2000 | Tomita et al. | ........... | 356/237.1 |

FOREIGN PATENT DOCUMENTS

| JP | 07-294422 | 11/1995 | | |
| JP | 09-064136 | 3/1997 | | |
| JP | 09167791 A | * | 6/1997 | ........... H01L/21/66 |
| JP | 10-062355 | 3/1998 | | |
| JP | 10-253546 | 9/1998 | | |
| JP | 10-293101 | 11/1998 | | |
| JP | 11-237225 | 8/1999 | | |

OTHER PUBLICATIONS

"Non–Destructive, Non–Contacting Test of Si Wafers by Thermoreflectance," Feb. 1, 1987, IBM Technical Disclosure Bulletin, vol. 29, Issue No. 9, pp. 4105–4113.*

* cited by examiner

Primary Examiner—Zander V. Smith
Assistant Examiner—Gordon J. Stock, Jr.
(74) Attorney, Agent, or Firm—Foley & Lardner LLP (57) ABSTRACT

The depth and a relative dimensional factor of a defect present in the interior of a silicon wafer are measured, and the number of such defects is calculated. A laser beam having a larger energy than the band gap of silicon is radiated obliquely to the semiconductor wafer and a scattered beam from a defect present in a subsurface layer of the wafer is detected by an image pick-up device. The temperature of the wafer is changed to at least two temperatures of $T_1$ and $T_2$ or to any one of plural temperatures by means of a heater and the intensity of a scattered beam is measured. It is taken into account that the light absorbance of silicon and the penetration depth of light in silicon vary depending on temperature, to determine the depth and a relative dimensional factor of an internal defect which causes scattering of light, as well as the number of such crystal defects.

19 Claims, 6 Drawing Sheets

WAFER DEFECT MEASURING METHOD AND APPARATUS

TECHNICAL FIELD OF THE INVENTION

The present invention relates to a defect measuring method and apparatus for an object to be measured. Particularly, the present invention is concerned with a defect measuring method suitable as a method for measuring and evaluating defects in crystal present in a surface layer of a semiconductor wafer, as well as an apparatus using the method.

RELATED ART

Heretofore, a method and an apparatus for non-destructively measuring defects in crystal present in a surface layer of a semiconductor wafer have been publicly known.

For example, for the observation of defects present in a surface layer portion not deeper than 5 $\mu$m, there has been made available a visible laser scattering tomography, for example, such as MO521 of Mitsui-Kinzoku-Kozan. According to this tomography, it is possible to observe defects up to a depth of 5 $\mu$m on an average from silicon wafers, but the depth and size of each individual surface layer defect cannot be obtained.

Also, in Japanese Patent Laid Open No. 64136/97 there are disclosed a method and an apparatus for determining an intensity distribution of scattered beams which reflect actual sizes of defects present in a surface layer of a semiconductor wafer. According to this method, defects present in a semiconductor wafer are measured on the basis of scattered beams generated from these defects. More particularly, light having a silicon absorbing wavelength is radiated to the wafer from a light source through an optical system, allowing scattered light to be generated from the wafer. This scattered light,is received by a detector and the optical system. Such an operation is performed for the whole area of the wafer and the results of scanning are processed as defect indicating information by means of a computer. At this time there is made correction for eliminating the influence of light absorption by silicon. The results of measurement are corrected taking the attenuation rate of light into account.

There also has been proposed an apparatus wherein plural laser beams of different wavelengths are radiated to a wafer, and on the basis of a difference in absorbance between the wavelengths there is obtained a scattered light intensity which reflects the size of a defect or information relating to the depth of a defect from a polished specular surface.

If the conventional laser scattering tomography of a two-wavelength type is used for the same purpose, the depth of a defect up to 0.5 $\mu$m right beneath the surface of silicon wafer can be measured by utilizing the wavelength dependence of absorption coefficient. For example, in OSDA (optical shallow crystal defect analyzer) of Hitachi there are used two laser beams of 532 nm and 810 nm in wavelength.

According to the conventional infrared laser scattering tomography, it is possible to measure defects in silicon wafers present at a position deeper than about 10 $\mu$m from the surface, but the measurement at the shallower region is impossible. An example of laser beam wavelength is 1.06 $\mu$m.

The semiconductor wafer defect measuring method and apparatus disclosed in Japanese Patent Laid Open No. 64136/97 are for making correction with respect to a scattered light intensity distribution obtained by measurement and not for correcting the intensity of a scattered light with respect to each detect. Thus, the depth from a polished specular surface, as well as a relative dimensional factor, of each crystal defect cannot be measured.

On the other hand, in a measuring apparatus using plural laser beams of different wavelengths, the optical system used is complicated, which is very disadvantageous in point of detection accuracy and cost.

The above conventional apparatuses are lacking in a method for obtaining, with a high accuracy, information relating to the depths and sizes of defects present in a surface layer up to a depth of 10 $\mu$m from the surface. For example, it has been difficult to determine which of two defects is the larger.

In the case where a high accuracy is not so strictly required for the depth of a subsurface defect and it suffices roughly to know a defect density up to a certain depth, the measurement concerned can be effected by changing the laser wavelength. In this case, however, it is necessary to provide plural lasers in advance. Thus, this method is also compelled to use a complicated optical system, which is disadvantageous in point of detection sensitivity and cost.

SUMMARY OF THE INVENTION

It is an object of the present invention to provide a method and apparatus for measuring defects of an object (especially a semiconductor wafer) to be measured which method and apparatus can measure the depth of each individual defect and the number of defects in a non-destructive manner.

It is another object of the present invention to provide a semiconductor wafer defect measuring method and apparatus capable of comparing sizes of defects.

It is a further object of the present invention to provide a semiconductor wafer crystal defect measuring method and apparatus using an optical system not complicated, advantageous in point of detection sensitivity and cost, and capable of measuring defects in a non-destructive manner.

According to the present invention, crystal defect measuring method and apparatus for an object (especially a semiconductor wafer) to be measured are described in the appended claims. The defects include not only oxygen precipitates, but also voide defects, stacking faults and others that produce scattered beams upon receipt of laser beams.

The present invention is to improve a method and apparatus for non-destructively measuring defects present in a subsurface layer of an object to be measured.

According to the present invention, the phenomenon that the intensity of a scattered light varies depending on temperature is utilized, and the intensities of scattered beams are measured at two or more temperatures, thereby determining the depths of defects from the surface of an object (especially a semiconductor wafer) to be measured, as well as relative dimensional factors of the defects.

In the present invention, the phenomenon that the penetration depth of a laser beam varies depending on temperature is utilized, and the intensity of a scattered beam is measured at any of plural temperatures, thereby determining the number of crystal defects present in a region from the wafer surface up to an arbitrary depth.

In a preferred example of the defect measuring method and apparatus according to the present invention, the intensities of scattered beams of a laser at two or more temperatures of an object to be measured are measured, thereby determining the depths of defects from the surface of the object to be measured. In comparing the sizes of defects, the intensities of scattered beams of a laser at two or more temperatures of an object to be measured are measured to determine a relative dimensional factor of each defect in the object. In determining the number of defects, a laser beam is radiated to the surface of an object to be measured to scan the same surface and the intensity of scattered beam from the object is measured at any of plural temperatures of the object, thereby calculating the number of defects present in a region from the object surface up to an arbitrary depth. A typical and preferred example of the object to be measured is a semiconductor wafer, particularly a silicon wafer, provided the present invention is also applicable to other objects than wafer.

In one preferred mode for carrying out the present invention, the intensities of scattered beams of a single laser are measured at two or more temperatures, thereby measuring defects present in a surface layer of a semiconductor wafer in a non-destructive manner. For example, by measuring the intensities of scattered beams generated from defects in a semiconductor wafer at two different temperatures, there are determined the depths of defects from the surface of the wafer, as well as relative dimensional factors of these defects.

In another mode for carrying out the present invention, the intensity of a scattered beam of a single laser is measured at any of plural temperatures, thereby measuring a defect present in a surface layer of a semiconductor wafer in a non-destructive manner. For example, by measuring the intensity of a scattered beam at any of plural temperatures of a wafer, there is calculated the number of crystal defects present in a region from the wafer subsurface up to an arbitrary depth.

In a further mode for carrying out the present invention, the number of defects present in a first wafer subsurface layer and that present in a second wafer subsurface layer are measured at a first temperature ($T_1$) and a second temperature ($T_2$) higher than the first temperature, and the difference between the two is calculated to determine the number of crystal defects present in a third layer which results from exclusion of the second layer from the first layer. In this case, the third layer is present between the depth of the first layer and that of the second layer.

It is preferable that the wafer be heated or cooled with a heater or the like in an accurately temperature-controlled state by a temperature controller. By so doing, the wafer can be measured in a uniformly and accurately temperature-controlled state. The wafer temperature may be measured directly with a temperature sensor or may be detected by measuring the temperature of the heater and subsequent calculation based on the result of the measurement. There also may be adopted a method wherein the heater temperature is kept constant, and without measuring the wafer and heater temperatures for each wafer, the intensities of scattered beams at two or more temperatures are measured to determine the depths of defects from the wafer surface and relative dimensional factors of these defects. Further, there may be adopted a method wherein the heater temperature is kept constant, and upon reaching a steady state after putting a wafer in place, the intensity of a scattered beam at any of plural temperatures is measured without measuring the wafer and heater temperatures, thereby calculating the number of defects present in a region from the wafer surface up to an arbitrary depth.

According to the present invention, with only a single laser, an object to be measured is measured at different temperatures, whereby it is possible to measure the difference in intensity between scattered beams caused by the difference in temperature and determine depths and relative dimensional factors of defects.

According to the present invention, measurement is made while changing the temperature of an object to be measured with a single laser, and the difference in intensity of scattered beams caused by the difference in temperature is measured, whereby the number of defects in a specific depth area can be determined.

As to the wafer-heater relation, there may be adopted any of various modes.

For example, a wafer is heated with a single heater and is changed its temperature to two or more temperatures by changing the heater temperature.

Further, a wafer is heated with a single heater and is changed its temperature to two or more temperatures by changing the distance between the heater and the wafer.

Further, a wafer is heated with two heaters in a separate manner and is changed its temperature into two or more temperatures by making the heating temperatures of the two heaters different from each other.

In a further preferred mode for carrying out the present invention, a laser beam having a larger energy than the band gap of silicon is applied obliquely to the surface of a silicon wafer and a scattered beam from defects such as a oxygen precipitates present near the wafer surface is detected. Preferably, if defects present in the depth of about 5 $\mu$m from the surface are measured, the wavelength of the laser beam is about 680 nm. It is preferable that, in the depth more than 5 $\mu$m, the wavelength of the laser beam is long, while in the depth less than 5 $\mu$m, the wavelength of the laser beam is short. If a laser beam having a long wave-length is used, then the measuring area is wide, but the measuring accuracy is poor due to $\Delta\alpha$ reduction of temperature dependence on absorption coefficient of silicon.

In a still further mode for carrying out the present invention, a laser beam having a larger energy than the band gap of silicon is applied obliquely to the surface of a wafer at a first temperature ($T_1$) and the intensity of a scattered beam from a defect present near the wafer surface is detected, further, the laser beam is directed obliquely to the wafer surface at a second temperature ($T_2$) different from the first temperature ($T_1$) and the intensity of a scattered beam from a defect present near the wafer surface is detected, and on the basis of the difference in intensity between the two scattered beams at the first and second temperatures ($T_1$), ($T_2$) there is calculated the depth of a defect from the wafer surface.

In a wafer defect measuring apparatus in a preferred mode of the present invention, a silicon wafer is placed on a wafer rest, then a laser beam having a larger energy than the band gap of silicon is radiated to the wafer surface obliquely (e.g., at an angle near the Brewster angle), and a scattered beam from defects present in the wafer subsurface is detected. In this apparatus, the wafer rest is provided with a wafer temperature controller to keep the wafer at the same temperature by cooling or heating and the intensity of a scattered beam at any of plural wafer temperatures is measured, or the intensities of scattered beams at two or more wafer temperatures are measured and thereafter relative dimensional factors are obtained.

In another preferred mode according to the present invention, a heater for heating the wafer placed on the wafer rest is suitable for the temperature controller.

In the wafer defect measuring apparatus according to the present invention there may be used a heater or heaters in the following fashion.

(1) A wafer is heated by a single heater and the wafer temperature is changed to two or more temperatures by changing the heater temperature.

(2) While a heater is held at a predetermined temperature, and a wafer is heated by the heater and the wafer temperature is changed to two or more temperatures by changing the distance between the heater and the wafer.

(3) Two heaters are held at different temperatures and a wafer is heated by the two heaters in a separate manner.

Deriving Depth

Various methods are available for deriving the depth. Reference will first be made below to a simple method for deriving the depth referring to FIG. 3.

Figure 3:
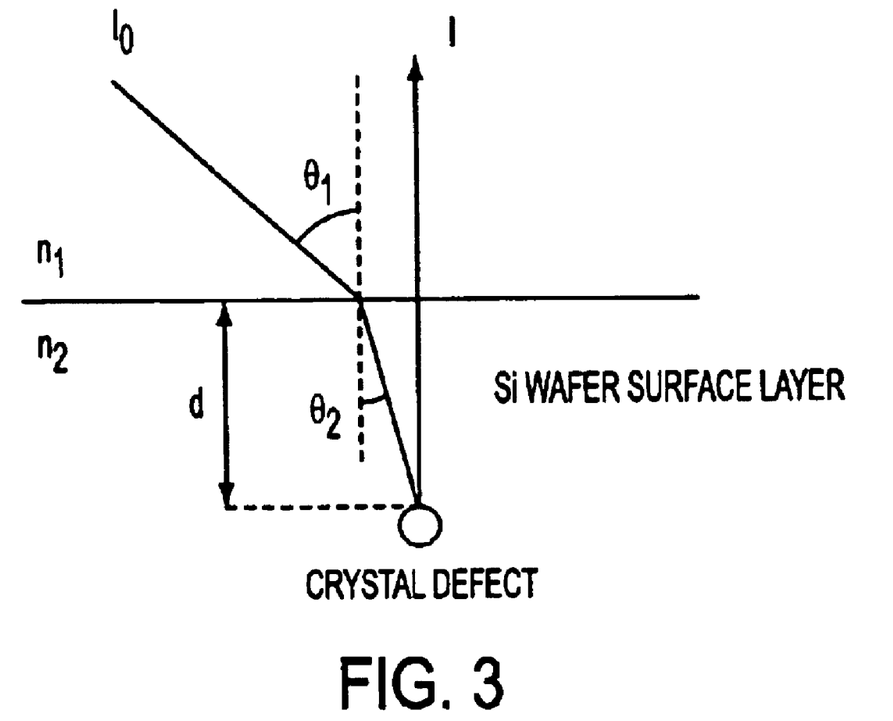
FIG. 3 is a diagram for explaining a principle of detecting the depth of a defect in a subsurface layer of a semiconductor wafer in the method according to the present invention.

In the case where a defect present in a certain depth, d, from the surface of a wafer has been detected, the intensity, I, of a scattered beam is determined by the following equation:

$$I = A\exp(-2\alpha d) \quad \text{(1)(Lambert-Beer's law)}$$

where $\alpha$ stands for an absorption coefficient of Si and A stands for the intensity of the scattered beam in an Si absorption-free condition. $I_0$ is a function of, for example, ① incident beam intensity, ② size and shape of the defect, ③ wavelength of incident beam, ④ dielectric constant of Si, and ⑤ dielectric constant of defect. Of these factors, ①, ②, and ③ are free of changes by temperature, and also as to ④ and ⑤, they undergo such small changes by temperature as can be ignored. Thus, in the equation (1), it is $\alpha$ that is considered to have a temperature dependence. If the absorption coefficient $\alpha$ of Si at $T_1°$ C. and that at $T_2°$ C. are assumed to be $\alpha_{T1}$ and $\alpha_{T2}$, respectively, these absorption coefficients are represented by the following equations:

$$I_{T1} = A\exp(-2\alpha_{T1}d) \quad (2)$$

$$I_{T2} = A\exp(-2\alpha_{T2}d) \quad (3)$$

where $I_{T1}$ and $I_{T2}$ stand for the intensities of scattered beams at $T_1°$ C. and $T_2°$ C., respectively.

From equations (2) and (3):

$$d = \ln(I_{T2}/I_{T1})/-2(\alpha_{T2}-\alpha_{T1}) = \ln(I_{T2}/I_{T1})/-2\Delta\alpha \quad (4)$$

$$(\Delta\alpha = \alpha_{T2} - \alpha_{T1})$$

From equation (2):

$$A = I_{T1}/\exp(-2\alpha_{T1}d) \quad (5)$$

Therefore, if $\alpha_{T1}$ and $\alpha_{T2}$ are known, or if $\alpha_{T1}$ and $\Delta\alpha$ are known, the depth d of a defect is determined from equation (4), and once d is thus known, the intensity of a scattered beam, A, in an Si absorption-free condition can be obtained from equation (5).

Further, equations (2) and (3) can be rewritten in such forms as will be shown below.

As shown in FIG. 3, if a defect is present at a depth of d in a surface layer of Si wafer, then by Snell's law:

$$n_1 \sin\theta_1 = n_2 \sin\theta_2$$

$$\sin\theta_2 = n_1/n_2 \sin\theta_1$$

$$\theta_2 = \sin^{-1}(\sin\theta_1 \times n_1/n_2)$$

The distance D at which light passes through Si may be written as follows:

$$D = d/\cos\theta_2 + d = d(1+1/\cos\theta_2) = d[1+1/\cos\{\sin^{-1}(\sin\theta_1 \times n_1/n_2)\}]$$

Thus, $$I = A\exp(-D\alpha) = A\exp(-\alpha[1+1/\cos\{\sin^{-1}(\sin\theta_1 \times n_1/n_2)\}]) \quad (6)$$

Deriving a Relative Dimensional Factor

Information on the actual size of a defect can be obtained, for example, by observing one defect which A was measured beforehand with use of a transmission electron microscope (TEM), obtaining A' of a crystal defect to be observed, and comparing the two.

Also in the calculation of depth, $\Delta\alpha$ may be used after calculating it on the basis of a measured value obtained with a TEM.

Thus, if a subsurface layer depth and size of a certain defect is once measured with a TEM, then on the basis of the thus-measured value it becomes possible to subsequently measure the depth and to compare the size of the defect in the object to be measured. Even if the dopant concentration of wafer somewhat changes, the measurement can be made with little influence.

The following description is now provided about a method for deriving the depth and a relative dimensional factor of a defect with a higher accuracy.

Given that the intensity of a scattered beam at room temperature (RT) and that at a high temperature (T° C.) with respect to a certain subsurface layer defect are $I_{RT}$ and $I_T$, respectively, the following equation is established for this defect in accordance with Lambert-Beer's law:

$$\ln(I_T/I_{RT}) = -2 \cdot \Delta\alpha \cdot d \quad (7)$$

where d is the depth of the crystal defect, $\Delta\alpha = \alpha_T - \alpha_{RT}$ {$\alpha_T$ is an absorption coefficient of Si at T° C. (at the incident laser wavelength), and $\alpha_{RT}$ is an absorption coefficient of Si at room temperature}.

① First, the depth, $d_{TEM}$, of a certain specific defect from the wafer surface is determined with a TEM or the like. Then, $I_{RT}$ and $I_T$ of this defect are obtained and substituted, together with $d_{TEM}$, into equation (7) to calculate $\Delta\alpha$.

② In subsequent measurement, if $I_{RT}$ and $I_T$ of another surface layer defect different from the above defect to be measured are measured, it is possible to determine the crystal depth d by using the $\Delta\alpha$ obtained in ①.

③ As to an estimated value of a relative dimensional factor, it is obtained in the following manner. The value of d obtained in ② is substituted into the following equation (8) or (9):

$$I_{RT} = A \cdot e^{-2\alpha_{RT}d} \quad (8)$$

$$I_T = A \cdot e^{-2\alpha_T d} \quad (9)$$

and $\alpha_{RT}$ or $\alpha_T$ using a theoretical value or a literature value, as well as $I_{RT}$ or $I_T$ of the object to be measured, are given to determine a relative dimensional factor A. The relative dimensional factor A is given as $A = I \cdot \beta \cdot T_t \cdot T_0 \cdot \delta$ where I is the intensity of the incident laser beam, $\beta$ is the apparatus function, $T_1$ is transmissivity of the incident beam, $T_0$ is transmissivity of scattered light, and $\delta$ is the cross section (at the surface), and t' is a reflectance at the surface (after scattering). Although shape, other than dimension, of a defect also contributes to the scattering efficiency, A does not simply depend on only the dimension of a defect, but here A is regarded as a relative dimensional factor in accordance with zero order approximation.

The thus-obtained defect depth d of the object to be measured proved to take a highly accurate value by calculation using $\Delta\alpha$ which has been obtained on the basis of a value measured with a TEM.

Calculation from the value of d thus obtained shows that the relative dimensional factor A also takes a highly accurate value. It is possible to not only obtain dimensional information of a certain defect but also compare the sizes of two defects.

Although in the above example the depth of a defect is first determined and thereafter a dimensional factor of the defect is obtained, the present invention is not limited to such an example.

Reference will now be made below to an example of obtaining a dimensional factor of a defect directly without obtaining the depth of the defect.

For example, deletion of d from equations (8) and (9) results in:

$$A = \exp\{(\alpha_T \ln I_{RT} - \alpha_{RT} \ln I_T)/(\alpha_T - \alpha_{RT})\} \tag{10}$$

If the intensities of scattered beams are measured at different temperatures with respect to defects of an object to be measured, the relative dimensional factor A can be calculated by substituting the result of the measurement into equation (10) together with $\alpha_{RT}$ and $\alpha_T$. In this case, it is not necessary to measure the defect depth of the object. By measuring the intensities of scattered beams at different temperatures it is possible to directly calculate values of the relative dimensional factor A in two defects. Comparison of the values permits comparison of two crystal defect sizes even without determining the depth of the defect concerned.

It is also possible to calculate the depth of the defect concerned by substituting the relative dimensional factor A thus obtained into equations (8) or (9) together with the intensity of scattered beam and absorption coefficient.

Calculating the Number of Defects

The following description is now provided about how to calculate the number of defects in accordance with the present invention.

In a single wavelength laser scattering tomography, the intensity of a scattered beam, $I_T$, from a certain surface layer crystal defect at a certain temperature T° C. can be expressed by the following equation in accordance with Lambert-Beer's low:

$$I_T = (I\beta T_i T_0 \delta) \cdot e^{-2\alpha(T)d} \tag{11}$$

where d is the depth of the defect, $\alpha(T)$ is the absorption coefficient at the wavelength of the incident laser beam and at the temperature of T, $I_0$ is the intensity of the incident laser beam, $\beta$ is the apparatus function, Ti is the transmissivity of the incident beam at the wafer surface, $T_0$ is the transmissivity of the scattered light at the wafer surface, and $\delta$ is the cross section (the function of refractive index, size and form of the defect, refractive index Si, and measurement direction).

These are put together as $A = I\beta T_i T_0 \delta$. In effect, the value A reflects the size of a defect. The value A which reflects the size of a defect can be obtained by the following equation using the intensity of a scattered beam, $I_T$, at the temperature T° C., absorption coefficient $\alpha(T)$, and depth d:

$$A = I_T / e^{-2\alpha(T)d} \tag{12}$$

where $\alpha(T)$ is a function of temperature. The higher the temperature, the larger the value of $\alpha(T)$, while the lower the temperature, the smaller the value of $\alpha(T)$. This is proportional to the fact that the higher the temperature, the shallower the penetration of a laser beam, while the lower the temperature, the deeper the penetration of the laser beam.

The present invention is based on the principle that the penetration depth of an incident beam changes with a change of wafer temperature. A detectable depth is controlled by controlling the wafer temperature to an arbitrary value. In this way the number of defects up to an arbitrary depth is determined.

This method does not measure an accurate depth or size of each defect. The depth of a defect can be obtained from equation (11), but in the present invention this may be considered to be one index of a measurable depth.

To make sure, a brief description will be given below of a method for calculating the depth d of each defect from the measurement of scattered beams at two temperatures and in accordance with a laser scattering tomography of a two-temperature type at a single wavelength.

In the case where one defect present at a certain depth d from the surface of a wafer at temperature T is measured, the intensity of a scattered beam, $I_T$, is expressed as follows in accordance with equation (12):

$$I_T = A\exp(-2\alpha(T)d) \tag{13} \text{(Lambert-Beer's low)}$$

Therefore, if the measurement is made at two temperatures of $T_1$° C. and $T_2$° C.:

$$I_{T1} = A\exp(-2\alpha(T_1)d) \tag{14}$$

$$I_{T2} = A\exp(-2\alpha(T_2)d) \tag{15}$$

where $I_{T1}$ is the intensity of a scattered beam at $T_1$° C. and $I_{T2}$ is the intensity of a scattered beam at $T_2$° C.

From equations (14) and (15):

$$d = \ln(I_{T2}/I_{T1})/-2(\alpha(T_2) - \alpha(T_1))$$

If $\Delta\alpha = \alpha(T_2) - \alpha(T_1)$, $$d = \ln(I_{T2}/I_{T1})/-2\Delta\alpha \tag{16}$$

Thus, if $\alpha(T_1)$ and $\alpha(T_2)$ are known, or if $\alpha_{Ti}$ and $\Delta\alpha$ are known, the depth d of a crystal defect is determined from equation (16), and once d is known, the value A which reflects the size of the crystal defect can be determined from equation (14) or (15).

In this invention, it is easy to measure scattered beams from a wafer because there is no need to move the wafer during the measurement at plural temperatures. The wafer may expand by heating and position of crystal defect may shift. But the shift can be adjusted easily for example, by program.

EMBODIMENTS

An embodiment of the present invention will be described below with reference to the drawings.

Figure 1:
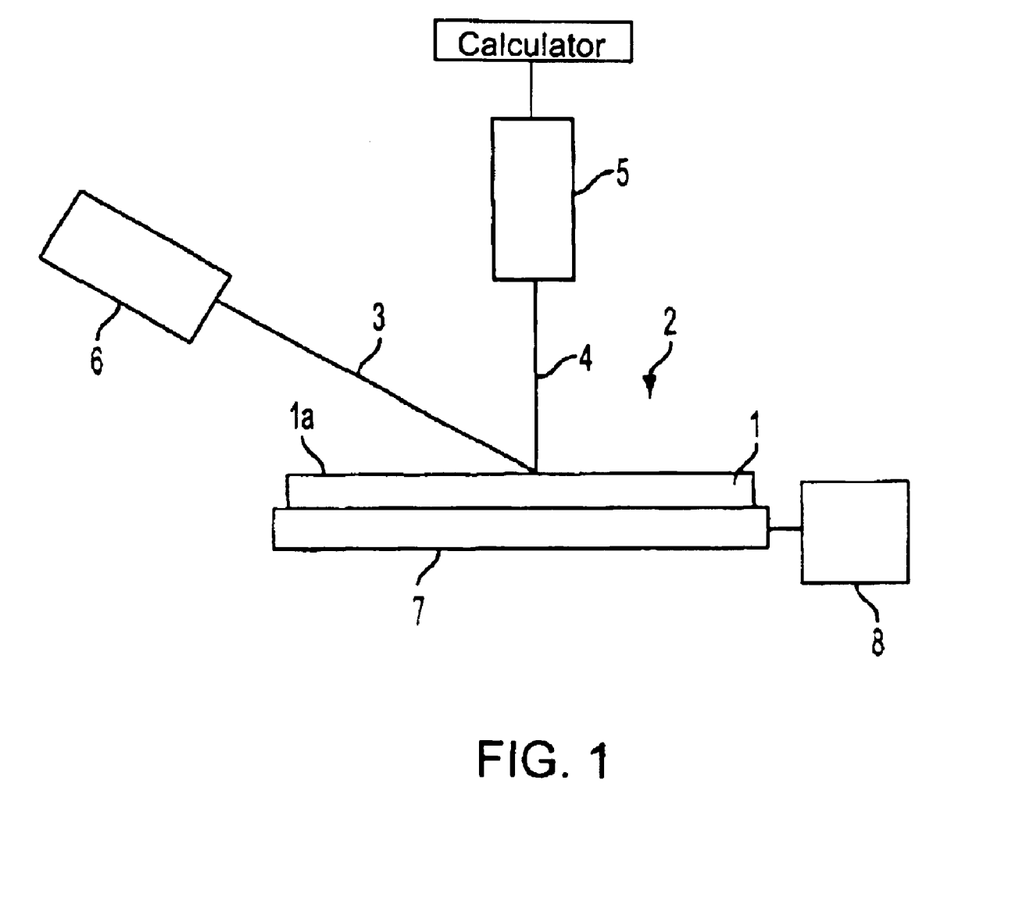
FIG. 1 is a schematic diagram showing a schematic configuration of a defect measuring apparatus for measuring crystal defects present in a subsurface layer of a semiconductor wafer according to an embodiment of the present invention.

In FIG. 1, a silicon wafer 1 is put on a wafer rest 2 in a wafer defect measuring apparatus of this embodiment. A laser beam 3 having a larger energy than the band gap of silicon is directed to a wafer surface 1a obliquely from a laser 6. For example, the laser beam 3 is incident at an angle near Brewster angle. If a defect such as an oxygen precipitate is present near the wafer surface 1a, a scattered beam 4 is generated from the defect and is detected by a detector 5. As an example of the detector 5 there is mentioned an image pick-up device or a microscope. The value detected by the detector 5 is sent to a calculator, in which a desired value is calculated.

The wafer rest 2 is provided with a heater 7 for heating the wafer 1 put on the wafer rest 2. The heater 7 is controlled its temperature by a temperature control panel 8.

In the measuring operation, the laser beam 3 having a larger energy than the band gap of silicon, which is generated by the laser 6, is incident on a polished specular surface of the semiconductor wafer 1 at an angle near Brewster angle, and the scattered beam 4 from a defect present in a subsurface layer of the polished specular surface is detected by the detector 5, e.g., a microscope, which is installed just above the wafer rest. The temperature of the silicon wafer 1 is changed into two different temperatures $T_1$ and $T_2$ by the heater 7, the intensity of the scattered beam 4 is detected by the detector 5, and changes in light absorbance of the silicon with temperatures are taken into consideration, thereby calculating a scattered beam intensity reflecting the depth and actual size of the internal defect which has generated the scattered beam 4. Alternatively, the temperature of the silicon wafer 1 is changed into any one of plural temperatures by the heater 7, the intensity of the scattered beam 4 is detected by the detector 5, and it is taken into account that the penetration depth of the laser beam varies depending on whether the temperature is high or low, thereby calculating the number of internal defects present up to the depth at which the scattered beam 4 was generated.

In one mode of shortening the measurement time for each wafer, when temperature $T_1$ is lower than temperature $T_2$, the measurement is made first at the lower temperature $T_1$ followed by measurement at the higher temperature $T_2$, and thereafter the wafer 1 is replaced. In this case, the measurement at the higher temperature $T_2$ covers only the places in which defects have been detected by the measurement at the lower temperature $T_1$.

According to the configuration of the embodiment illustrated in FIG. 1, the wafer 1 is heated by a single heater 7 and the temperature of the wafer 1 is changed into two or more temperatures by changing the heating temperature of the heater 7 with the temperature control panel 8.

The present invention is not limited to such a heater layout.

For example, there may be adopted a configuration wherein a single heater 7 is held at a predetermined temperature, and the distance between the heater 7 and the wafer 1 is changed to change the wafer temperature into two or more temperatures. In this case, by moving the heater 7 downward, with the wafer 1 fixed to the wafer rest 2, it is possible to change the distance between the heater and the wafer.

In one mode of shortening the operation time in this configuration, when temperature $T_1$ is lower than temperature $T_2$, first the heater 7 is moved to a predetermined lower position and measurement is made at the lower temperature $T_1$, then the heater 7 is moved to a predetermined upper position and measurement is made at the higher temperature $T_2$. Thereafter, the wafer 1 is replaced. In this case, it is preferred that the heater 7 be stopped at the predetermined upper position and be moved to the lower position just before the wafer temperature drops to the temperature $T_1$. Besides, the measurement at the higher temperature $T_2$ covers only the places in which crystal defects have been detected by the measurement at the lower temperature $T_1$.

Further, there may be adopted a configuration wherein two heaters 7 are held at temperatures different from each other, and the wafer 1 is heated by the two heaters 7 in a separate manner.

In the depth and relative dimensional factor measuring method according to the present invention there basically is employable the apparatus used in the foregoing wafer detect measuring method.

A TEM or the like is used in measuring the depth $d_{TEM}$ of a certain defect as a reference.

The measurement of scattered beams at different temperatures is conducted not only for a certain defect as a reference defect but also for defects found in the object to be measured. In this case, how to direct the laser beam 3 to the wafer surface 1a, how to detect the scattered beam 4, and how to change the wafer temperature are the same as in the foregoing wafer defect measuring method, so explanations thereof will here be omitted.

By changing the temperature of a CZ wafer (ρ: 10–9.6 Ω·cm, [Oi]=1.53–1.52×10$^{18}$ atoms/cm$^3$ [old ASTM]) which is used in measuring the number of defects, there is estimated a wafer penetration depth at each of various temperatures (23° C., 70° C., 150° C.) of a laser with a wavelength of 680 nm, as will be shown below. As to the temperature dependence of Si absorption coefficient, reference was made to G. E. Jellison, Jr., et al.'s literature (appl. Phys. Lett. 41, 180 (1982)). An absorption coefficient, α(T) (1/cm), of Si for light with a wavelength of 680 nm at temperature T(K) is roughly described as follows:

$$\alpha(T)=1.49\times10^3\times\exp(T/430) \tag{17}$$

The distance $d_p$ (μm) required for attenuation to 1/e of light introduced into Si is:

$$d_p(T)=10000/\alpha(T) \tag{18}$$

At temperatures of 23° C., 70° C., and 150° C., the following $d_p$ values are obtained in accordance with equations (17) and (18):

$$d_p(23)=10000/\alpha(23)=10000/2966=3.34 \text{ (μm)}$$

$$d_p(70)=10000/\alpha(70)=10000/3308=3.02 \text{ (μm)}$$

$$d_p(150)=10000/\alpha(150)=10000/3985=2.51 \text{ (μm)}$$

Thus, it is presumed that the attenuation rate of light changes due to changes in absorption coefficient caused by changing of temperature and that a change of a measurable defect depth results.

EXAMPLE 1

Measuring the Depth of a Defect

Using the apparatus shown in FIG. 1, a laser beam (about 1.8 eV) having a wavelength of 680 nm was applied to a polished specular surface of Si wafer (Si band gap: 1.12 eV) at an angle near Brewster angle (73.7°) and the intensities of scattered beams from defects present in a wafer subsurface layer of a depth corresponding approximately to the penetration depth (about 3 μm) of the laser beam were measured. Particularly, the intensities of scattered beams at Si wafer temperatures of 23° C. and 83° C. were measured.

In the measurement, the wafer temperature was controlled by means of a heater which was in contact with the wafer, and the wafer temperature was checked using a thermocouple.

Figure 4:
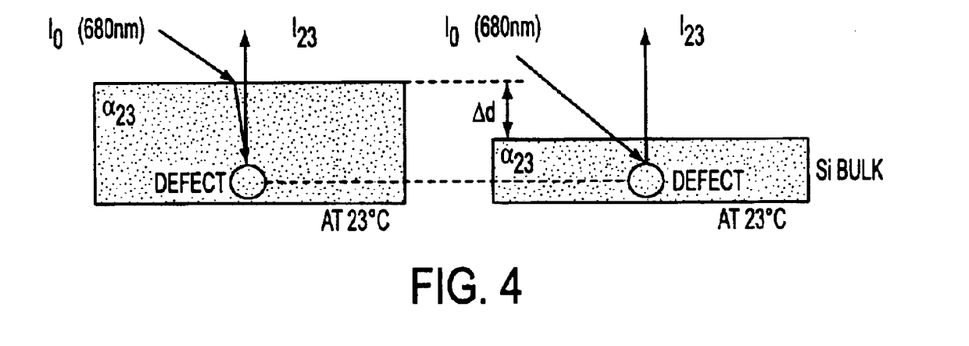
FIG. 4 is a diagram explaining measurement of the intensities of scattered beams from the same defect before and after polishing $\Delta d$ ($\mu m$)

As shown in FIG. 4, the scattered beam intensity, $I_{23}$, of a certain defect at 23° C. is measured and thereafter polishing is performed about Δd (cm) from the surface, followed by re-measurement of the scattered beam intensity, $I_{23}'$, of the same crystal defect. In this case, the absorption coefficient $\alpha_{23}$ of Si at 23° C. is represented by the following equation:

$$\alpha_{23}=(\ln(I_{23}/I_{23}'))/(-2\cdot\Delta d). \tag{1}$$

The results of actual measurement using the above method are shown in Table 1, from which results $\alpha_{23}$ was determined to be approximately 2200 cm$^{-1}$.

After the intensities of scattered beams $I_{23}$ and $I_{83}$ at temperatures of 23° C. and 83° C. had been measured, the defect depth d was determined using a TEM. In this case, $\Delta\alpha(=\alpha_{83}-\alpha_{23})$ is expressed by the following equation:

$$\Delta\alpha=\ln(I_{83}/I_{23})/(-2/d)$$

Table 2 shows the results of having actually determined Δα by the above method, from which results a mean value of Δα is determined to be about 705 cm$^{-1}$. In this experiment there could be measured only up to two defects, but it is expected that a more accurate value of Δα will be obtained if the number of measurements is increased.

TABLE 2

|  | $I_{23}$ | $I_{83}$ | Depth by TEM, d (μm) | Δα (cm$^{-1}$) |
|---|---|---|---|---|
| Crystal defect A | 477 | 185 | 6.5 | 729 |
| Crystal defect B | 604 | 301 | 5.1 | 681 |

The defect depth d is determined as follows from the ratio, $I_{83}/I_{23}$, of the scattered beam intensity $I_{83}$ at 83° C. to the scattered beam intensity $I_{23}$ at 23° C. and also from the foregoing Δα:

$$d=\ln(I_{83}/I_{23})/(-2\Delta\alpha)$$

The intensity of a scattered beam $I_0$ (equal to A in equation (1)) based on the assumption that the depth from the surface of a detected defect is zero, which is for eliminating the influence of light absorption of Si, is presumed to reflect information on the actual size of the defect. The scattered beam intensity $I_0$ is given as:

$$I_0=I_{23}/\exp(-2\times\alpha_{23}\times d)$$

If the measured $I_{23}$ is 100 and $I_{83}$ is 80, the ratio $I_{83}/I_{23}$ is 0.8, the depth d of the defect is $1.58\times10^{-4}$ cm, and the scattered beam intensity $I_0$ is determined to be 246, assuming that the defect is present on the wafer surface. Since this value is a corrected value with respect to the attenuation of light which poses a problem in case of a defect being present in the interior of Si, it can be utilized in comparing the sizes (dimensions) of crystal defects present at different depths.

The ratio ($I_{83/23}=I_{83}/I_{23}$) of the scattered beam intensity $I_{83}$ at 83 to the scattered beam intensity $I_{23}$ at 23° C., which were measured actually, is shown in Table 3. Also shown in Table 3 are the scattered beam intensity $I_0$ based on the assumption that the depth from the surface of a defect is zero, which was calculated in accordance with the method of the present invention, as well as the depth d from the surface.

TABLE 1

| Wafer No. lo. |  | 1 | 2 | 3 | 4 | 5 | 6 | 7 | 8 | 9 |
|---|---|---|---|---|---|---|---|---|---|---|
| Allowance for polishing (μm) |  | 5.42 | 4.88 | 5.26 | 4.72 | 5.04 | 5.00 | 5.73 | 5.05 | 6.02 |
| Absorption | AVE | 2260 | 1926 | 2118 | 2147 | 2120 | 2220 | 2225 | 2304 | 2323 |
| coefficient | STD | 166 | 257 | 264 | 264 | 293 | 275 | 235 | 241 | 387 |
| α | MAX | 2435 | 2285 | 2723 | 2881 | 2890 | 2843 | 2697 | 2861 | 2928 |
| (room temperature) | MIN | 1928 | 1384 | 1470 | 1697 | 1737 | 1653 | 1794 | 1873 | 1078 |

TABLE 3

| Crystal defect No. | Scattered beam intensity (I23) at room temperature 23° C. | Scattered beam intensity (I83) at 83° C. | I83/I23 | Depth, d (cm) | Scattered beam intensity (I0) at depth 0 |
|---|---|---|---|---|---|
| 1 | 162 | 118 | 0.728 | 2.2E-04 | 436 |
| 2 | 832 | 554 | 0.688 | 2.9E-04 | 2963 |
| 3 | 5489 | 4933 | 0.899 | 7.6E-05 | 7663 |
| 4 | 282 | 108 | 0.383 | 6.8E-04 | 5640 |
| 5 | 188 | 123 | 0.661 | 2.9E-04 | 678 |
| 6 | 97 | 34 | 0.351 | 7.4E-04 | 2558 |
| 7 | 202 | 138 | 0.673 | 2.8E-04 | 694 |
| 8 | 835 | 305 | 0.480 | 5.2E-04 | 6295 |
| 9 | 445 | 205 | 0.481 | 5.5E-04 | 4977 |
| 10 | 138 | 49 | 0.360 | 7.2E-04 | 3289 |
| 11 | 81 | 38 | 0.469 | 5.4E-04 | 859 |
| 12 | 450 | 270 | 0.600 | 3.6E-04 | 2212 |
| 13 | 188 | 108 | 0.574 | 3.9E-04 | 1060 |
| 14 | 877 | 676 | 0.771 | 1.8E-04 | 1971 |
| 15 | 1385 | 731 | 0.528 | 4.5E-04 | 10167 |
| 16 | 94 | 34 | 0.362 | 7.2E-04 | 2248 |
| 17 | 309 | 163 | 0.527 | 4.5E-04 | 2276 |
| 18 | 485 | 200 | 0.412 | 6.3E-04 | 7726 |
| 19 | 197 | 125 | 0.635 | 3.2E-04 | 815 |
| 20 | 289 | 139 | 0.482 | 5.2E-04 | 2818 |
| 21 | 2128 | 1676 | 0.788 | 1.7E-04 | 4484 |
| 22 | 1415 | 972 | 0.687 | 2.7E-04 | 4569 |
| 23 | 30 | 22 | 0.733 | 2.2E-04 | 79 |
| 24 | 305 | 201 | 0.660 | 3.0E-04 | 1117 |
| 25 | 686 | 472 | 0.688 | 2.7E-04 | 2205 |
| 26 | 745 | 472 | 0.834 | 3.2E-04 | 3091 |
| 27 | 159 | 88 | 0.553 | 4.2E-04 | 1007 |
| 28 | 454 | 427 | 0.940 | 4.4E-05 | 551 |
| 29 | 1362 | 850 | 0.624 | 3.3E-04 | 5933 |

TABLE 3-continued

| Crystal defect No. | Scattered beam intensity (I23) at room temperature 23° C. | Scattered beam intensity (I83) at 83° C. | I83/I23 | Depth, d (cm) | Scattered beam intensity (I0) at depth 0 |
|---|---|---|---|---|---|
| 30 | 805 | 791 | 0.983 | 1.2E-05 | 849 |
| 31 | 61 | 34 | 0.557 | 4.1E-04 | 378 |
| 32 | 2099 | 1685 | 0.803 | 1.6E-04 | 4168 |
| 33 | 376 | 199 | 0.529 | 4.5E-04 | 2749 |
| 34 | 986 | 731 | 0.741 | 2.1E-04 | 2509 |
| 35 | 141 | 78 | 0.553 | 4.2E-04 | 895 |
| 36 | 468 | 263 | 0.581 | 4.1E-04 | 2834 |
| 37 | 976 | 845 | 0.866 | 1.0E-04 | 1530 |
| 38 | 138 | 100 | 0.725 | 2.3E-04 | 377 |
| 39 | 2040 | 1676 | 0.822 | 1.4E-04 | 3765 |
| 40 | 63 | 30 | 0.566 | 4.0E-04 | 313 |
| 41 | 75 | 56 | 0.747 | 2.1E-04 | 187 |
| 42 | 850 | 717 | 0.844 | 1.2E-04 | 1441 |
| 43 | 1548 | 1223 | 0.791 | 1.7E-04 | 3213 |
| 44 | 68 | 44 | 0.647 | 3.1E-04 | 265 |
| 45 | 254 | 163 | 0.642 | 3.1E-04 | 1013 |
| 46 | 43 | 39 | 0.907 | 6.9E-04 | 58 |
| 47 | 855 | 303 | 0.462 | 5.5E-04 | 7272 |
| 48 | 809 | 690 | 0.853 | 1.1E-04 | 1327 |
| 49 | 110 | 37 | 0.336 | 7.7E-04 | 3296 |
| 50 | 4705 | 3654 | 0.777 | 1.8E-04 | 10358 |
| 51 | 314 | 176 | 0.560 | 4.1E-04 | 1924 |
| 52 | 513 | 277 | 0.540 | 4.4E-04 | 3516 |
| 53 | 50 | 30 | 0.600 | 3.6E-04 | 246 |
| 54 | 177 | 91 | 0.514 | 4.7E-04 | 1411 |
| 55 | 1623 | 1592 | 0.981 | 1.4E-05 | 1723 |
| 56 | 655 | 290 | 0.442 | 5.8E-04 | 8337 |
| 57 | 1169 | 785 | 0.672 | 2.8E-04 | 4046 |
| 58 | 472 | 205 | 0.434 | 5.9E-04 | 6360 |
| 59 | 417 | 335 | 0.803 | 1.6E-04 | 828 |
| 60 | 104 | 46 | 0.442 | 5.8E-04 | 1326 |
| 61 | 622 | 485 | 0.781 | 1.8E-04 | 1346 |
| 62 | 66 | 21 | 0.318 | 8.1E-04 | 2352 |
| 63 | 813 | 713 | 0.878 | 9.3E-05 | 1222 |
| 64 | 845 | 727 | 0.880 | 1.1E-04 | 1355 |
| 65 | 818 | 618 | 0.755 | 2.0E-04 | 1967 |
| 66 | 178 | 106 | 0.596 | 3.7E-04 | 897 |
| 67 | 193 | 147 | 0.762 | 1.9E-04 | 451 |
| 68 | 161 | 76 | 0.472 | 5.3E-04 | 1676 |
| 69 | 854 | 682 | 0.799 | 1.6E-04 | 1721 |
| 70 | 210 | 195 | 0.929 | 5.3E-05 | 265 |
| 71 | 199 | 180 | 0.905 | 7.1E-05 | 272 |
| 72 | 1223 | 854 | 0.698 | 2.6E-04 | 3757 |
| 73 | 1077 | 859 | 0.798 | 1.6E-04 | 2180 |
| 74 | 129 | 73 | 0.566 | 4.0E-04 | 762 |
| 75 | 77 | 39 | 0.506 | 4.8E-04 | 643 |
| 76 | 877 | 513 | 0.585 | 3.8E-04 | 4678 |
| 77 | 329 | 141 | 0.429 | 6.0E-04 | 4601 |
| 78 | 191 | 134 | 0.702 | 2.5E-04 | 577 |
| 79 | 1123 | 854 | 0.760 | 1.9E-04 | 2644 |
| 80 | 2026 | 1638 | 0.809 | 1.5E-04 | 3926 |
| 81 | 208 | 135 | 0.649 | 3.1E-04 | 801 |
| 82 | 29 | 26 | 0.897 | 7.7E-04 | 41 |
| 83 | 174 | 57 | 0.328 | 7.5E-04 | 5663 |
| 84 | 577 | 458 | 0.794 | 1.6E-04 | 1183 |
| 85 | 62 | 21 | 0.339 | 7.7E-04 | 1818 |
| 86 | 1744 | 1638 | 0.940 | 4.4E-05 | 2119 |
| 87 | 805 | 554 | 0.688 | 2.7E-04 | 2583 |
| 88 | 345 | 175 | 0.508 | 4.8E-04 | 2859 |
| 89 | 1185 | 881 | 0.744 | 2.1E-04 | 2986 |
| 90 | 1813 | 1585 | 0.874 | 9.5E-05 | 2757 |
| 91 | 94 | 32 | 0.340 | 7.6E-04 | 2713 |
| 92 | 137 | 29 | 0.212 | 1.1E-03 | 17418 |
| 93 | 168 | 164 | 0.976 | 1.7E-05 | 181 |
| 94 | 141 | 95 | 0.674 | 2.8E-04 | 483 |
| 95 | 194 | 127 | 0.655 | 3.0E-04 | 728 |
| 96 | 73 | 25 | 0.342 | 7.6E-04 | 2068 |
| 97 | 346 | 163 | 0.471 | 5.3E-04 | 3615 |
| 98 | 89 | 41 | 0.461 | 5.5E-04 | 1000 |
| 99 | 70 | 29 | 0.414 | 6.2E-04 | 1095 |
| 100 | 5199 | 3755 | 0.722 | 2.3E-04 | 14348 |
| 101 | 293 | 211 | 0.720 | 2.3E-04 | 815 |
| 102 | 322 | 216 | 0.671 | 2.8E-04 | 1120 |
| 103 | 93 | 28 | 0.301 | 8.5E-04 | 3938 |
| 104 | 335 | 306 | 0.913 | 6.5E-05 | 445 |
| 105 | 257 | 216 | 0.840 | 1.2E-04 | 443 |
| 106 | 276 | 170 | 0.617 | 3.4E-04 | 1244 |
| 107 | 348 | 167 | 0.480 | 5.2E-04 | 3439 |
| 108 | 211 | 122 | 0.678 | 3.9E-04 | 1166 |
| 109 | 159 | 77 | 0.484 | 5.1E-04 | 1528 |
| 110 | 404 | 200 | 0.495 | 5.0E-04 | 3811 |
| 111 | 526 | 404 | 0.767 | 1.9E-04 | 1205 |
| 112 | 123 | 53 | 0.431 | 6.0E-04 | 1702 |
| 113 | 1615 | 963 | 0.596 | 3.7E-04 | 8123 |
| 114 | 1492 | 1085 | 0.727 | 2.3E-04 | 4039 |
| 115 | 127 | 65 | 0.512 | 4.8E-04 | 1027 |
| 116 | 559 | 333 | 0.595 | 3.7E-04 | 2821 |
| 117 | 668 | 417 | 0.624 | 3.3E-04 | 2904 |
| 118 | 302 | 276 | 0.914 | 6.4E-05 | 399 |
| 119 | 1138 | 927 | 0.814 | 1.5E-04 | 2160 |
| 120 | 1703 | 1377 | 0.808 | 1.8E-04 | 3308 |
| 121 | 513 | 464 | 0.904 | 7.1E-05 | 702 |
| 122 | 51 | 31 | 0.608 | 3.5E-04 | 241 |
| 123 | 257 | 132 | 0.513 | 4.7E-04 | 2062 |
| 124 | 1492 | 1231 | 0.825 | 1.4E-04 | 2723 |
| 125 | 431 | 194 | 0.450 | 5.7E-04 | 5199 |
| 126 | 717 | 491 | 0.684 | 2.7E-04 | 2342 |
| 127 | 927 | 777 | 0.838 | 1.3E-04 | 1608 |
| 128 | 267 | 157 | 0.588 | 3.8E-04 | 1398 |
| 129 | 94 | 65 | 0.691 | 2.6E-04 | 297 |
| 130 | 873 | 590 | 0.677 | 2.8E-04 | 2954 |
| 131 | 330 | 283 | 0.889 | 8.4E-05 | 477 |
| 132 | 99 | 41 | 0.414 | 8.3E-04 | 1550 |
| 133 | 57 | 24 | 0.421 | 6.1E-04 | 848 |
| 134 | 805 | 481 | 0.598 | 3.6E-04 | 3996 |
| 135 | 614 | 586 | 0.956 | 3.2E-05 | 707 |
| 136 | 672 | 450 | 0.689 | 2.8E-04 | 2353 |
| 137 | 1400 | 945 | 0.675 | 2.8E-04 | 4773 |
| 138 | 80 | 61 | 0.763 | 1.9E-04 | 188 |
| 139 | 26 | 39 | 1.500 | -2.9E-04 | 7 |
| 140 | 87 | 39 | 0.488 | 5.7E-04 | 1064 |
| 141 | 1515 | 1015 | 0.670 | 2.8E-04 | 5288 |
| 142 | 1646 | 1262 | 0.766 | 1.9E-04 | 3777 |
| 143 | 98 | 42 | 0.429 | 6.0E-04 | 1379 |
| 144 | 213 | 116 | 0.545 | 4.3E-04 | 1419 |
| 145 | 176 | 161 | 0.915 | 6.3E-05 | 232 |
| 146 | 1262 | 740 | 0.587 | 3.8E-04 | 6653 |
| 147 | 92 | 44 | 0.478 | 5.2E-04 | 919 |
| 148 | 67 | 32 | 0.478 | 5.2E-04 | 672 |
| 149 | 105 | 37 | 0.352 | 7.4E-04 | 2721 |
| 150 | 110 | 99 | 0.900 | 7.5E-05 | 153 |
| 151 | 71 | 22 | 0.310 | 8.3E-04 | 2749 |
| 152 | 713 | 822 | 0.872 | 9.7E-05 | 1094 |
| 153 | 400 | 201 | 0.503 | 4.9E-04 | 3409 |
| 154 | 131 | 80 | 0.611 | 3.5E-04 | 610 |
| 155 | 1700 | 1469 | 0.884 | 1.0E-04 | 2680 |
| 156 | 1146 | 904 | 0.789 | 1.7E-04 | 2403 |

Figure 2:
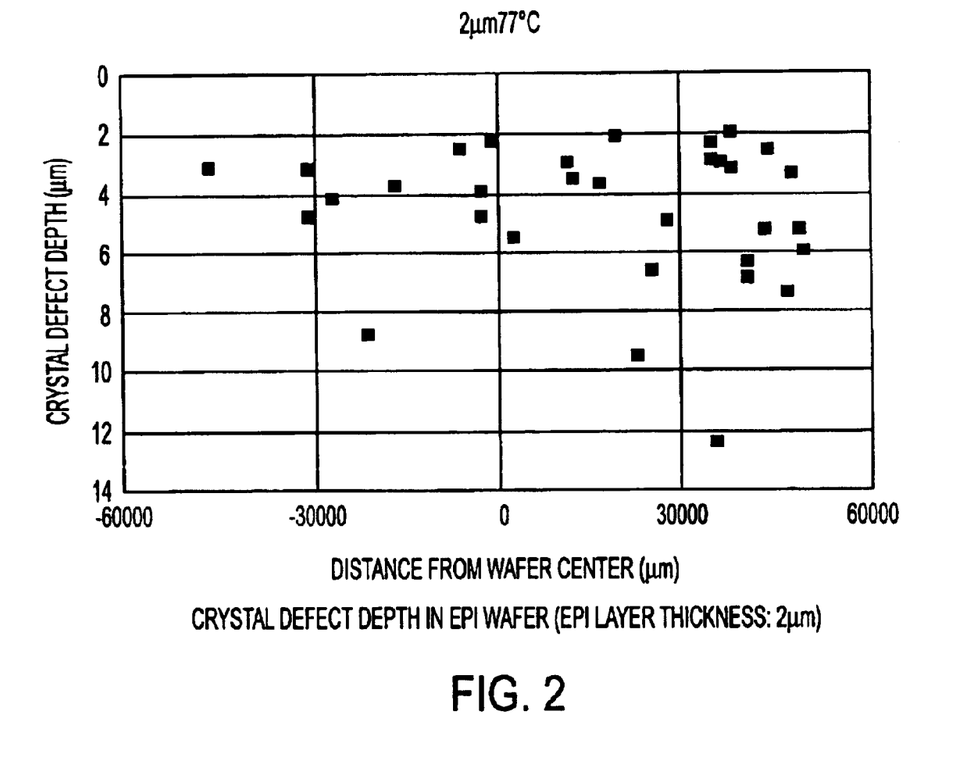
FIG. 2 is a diagram of an example showing at what depths in a surface layer of a semiconductor wafer defects are present, in a method according to the present invention.

FIG. 2 illustrates depths of crystal defects present in a subsurface layer of a semiconductor wafer measured by the method of the present invention. When an epitaxial layer 2 μm thick was formed on the wafer surface and depths of crystal defects were measured, there were obtained such results as shown in FIG. 2. In the same figure, small black square marks indicate at what depths from the surface defects are present. In the region up to the depth of 2 μm from the epi layer surface there was recognized no crystal defect. Most of crystal defects were present in the region of depths 2–8 μm from the epitaxial layer surface. Two defects were present in the region of 8–10 μm from the epitaxial layer surface. The presence of one defect was recognized in the region 12–14 μm deep from the epitaxial layer surface and at a distance of 30,000–60,000 μm from the wafer center.

The first temperature ($T_1$) and the second temperature ($T_2$) are not limited to the foregoing temperatures.

EXAMPLE 2

Measuring a Relative Dimensional Factor

Using the apparatus shown in FIG. 1, a laser beam (about 1.8 eV) having a wavelength of 680 nm was applied to a polished specular surface of Si wafer (band gap of Si: 1.12 eV) at an angle near Brewster angle (73.7°) and the intensity of a scattered beam generated from a defect present in a subsurface layer of the wafer corresponding to approximately the penetration depth (about 3 µm) of the laser beam was measured. Particularly, scattered beam intensities at Si wafer temperatures of 23° C. and 70° C. were measured.

In the measurement, the wafer temperature was controlled with the heater disposed in contact with the wafer and was checked with a radiation thermometer. Absorption coefficient $\alpha_{23}$ of Si for the laser beam of wavelength 680 nm at 23° C. was 2322 cm$^{-1}$ and that $\alpha_{70}$ at 70° C. was 2903 cm$^{-1}$, with the difference being $\Delta\alpha = \alpha_{70} - \alpha_{23} = 581$ cm$^{-1}$. Although $\alpha_{70}$, $\alpha_{23}$ are calculated on the basis of prior art documents, they can be calculated as in the Example 1 for the accuracy purpose.

The defect depth d is determined as follows from the ratio ($I_{70/23} = I_{70}/I_{23}$) of the scattered beam intensity $I_{70}$ at 70° C. to the scattered beam intensity $I_{23}$ at 23° C. and also from the foregoing $\Delta\alpha$:

$$d = \ln(I_{70/23})/(-2\Delta\alpha)$$

The scattered beam intensity $I_0$ (is equal to A in equation (1)) based on the assumption that the depth from the surface of a detected defect is zero, which is for eliminating the influence of light absorption of Si, is presumed to reflect information on the size of the defect. The scattered beam intensity $I_0$ is given as:

$$I_0 = I_{23}/\exp(-2 \times \alpha_{23} \times d)$$

If the measured $I_{23}$ is 100 and $I_{70}$ is 80, the ratio $I_{70/23}$ is 0.8, the depth d of the defect is $1.92 \times 10^{-4}$ cm, and the scattered beam intensity $I_0$ is determined to be 244, assuming that the defect is present on the wafer surface. Since this value is a corrected value with respect to the attenuation of light which poses a problem in case of a defect being present in the interior of Si, it can be utilized in comparing the sizes (dimensions) of defects present at different depths.

The ratio, $I_{70/23} = I_{70}/I_{23}$, of the scattered beam intensity $I_{70}$ at 70° C. to the scattered beam intensity $I_{23}$ at 23° C., which were measured actually, is shown in Table 4. Also shown in Table 4 are the scattered beam intensity $I_0$ based on the assumption that the depth from the surface of a defect is zero, which was measured in accordance with the method of the present invention, as well as the depth d from the surface.

TABLE 4

| Crystal defect No. | Scattered beam intensity ($I_{23}$) at 23° C. | Scattered beam intensity ($I_{70}$) at 70° C. | $I_{70}/I_{23}$ | Depth of crystal defect (cm) | Scattered beam intensity ($I_0$) at depth 0 |
|---|---|---|---|---|---|
| 1 | 310 | 273 | 0.881 | 1.09E-04 | 515 |
| 2 | 725 | 685 | 0.945 | 4.88E-05 | 910 |
| 3 | 38 | 22 | 0.579 | 4.70E-04 | 338 |
| 4 | 244 | 146 | 0.598 | 4.42E-04 | 1900 |

TABLE 4-continued

| Crystal defect No. | Scattered beam intensity ($I_{23}$) at 23° C. | Scattered beam intensity ($I_{70}$) at 70° C. | $I_{70}/I_{23}$ | Depth of crystal defect (cm) | Scattered beam intensity ($I_0$) at depth 0 |
|---|---|---|---|---|---|
| 5 | 123 | 56 | 0.455 | 6.77E-04 | 2855 |
| 6 | 410 | 313 | 0.763 | 2.32E-04 | 1206 |
| 7 | 563 | 356 | 0.632 | 3.94E-04 | 3516 |
| 8 | 1091 | 838 | 0.768 | 2.27E-04 | 3137 |
| 9 | 243 | 139 | 0.572 | 4.81E-04 | 2265 |
| 10 | 303 | 219 | 0.723 | 2.79E-04 | 1109 |
| 11 | 236 | 167 | 0.708 | 2.98E-04 | 940 |
| 12 | 92 | 63 | 0.685 | 3.26E-04 | 418 |
| 13 | 47 | 19 | 0.404 | 7.79E-04 | 1754 |
| 14 | 660 | 573 | 0.868 | 1.22E-04 | 1161 |
| 15 | 99 | 52 | 0.525 | 5.54E-04 | 1298 |
| 16 | 270 | 155 | 0.574 | 4.78E-04 | 2481 |
| 17 | 71 | 29 | 0.408 | 7.71E-04 | 2543 |
| 18 | 310 | 265 | 0.855 | 1.35E-04 | 580 |
| 19 | 94 | 32 | 0.340 | 9.27E-04 | 6973 |
| 20 | 695 | 570 | 0.820 | 1.71E-04 | 1535 |
| 21 | 173 | 77 | 0.445 | 6.97E-04 | 4396 |
| 22 | 56 | 35 | 0.625 | 4.04E-04 | 366 |
| 23 | 96 | 56 | 0.583 | 4.64E-04 | 828 |
| 24 | 290 | 164 | 0.566 | 4.91E-04 | 2830 |
| 25 | 895 | 595 | 0.665 | 3.51E-04 | 4575 |
| 26 | 915 | 805 | 0.880 | 1.10E-04 | 1527 |
| 27 | 213 | 100 | 0.469 | 6.51E-04 | 4373 |
| 28 | 373 | 280 | 0.751 | 2.47E-04 | 1174 |
| 29 | 323 | 243 | 0.752 | 2.45E-04 | 1007 |
| 30 | 941 | 822 | 0.874 | 1.16E-04 | 1615 |
| 31 | 64 | 36 | 0.563 | 4.95E-04 | 638 |
| 32 | 276 | 234 | 0.848 | 1.42E-04 | 534 |
| 33 | 280 | 261 | 0.932 | 6.05E-05 | 371 |
| 34 | 137 | 98 | 0.715 | 2.88E-04 | 523 |
| 35 | 91 | 46 | 0.505 | 5.87E-04 | 1390 |
| 36 | 785 | 493 | 0.628 | 4.00E-04 | 5038 |
| 37 | 785 | 590 | 0.752 | 2.46E-04 | 2458 |
| 38 | 3236 | 3014 | 0.931 | 6.12E-05 | 4301 |
| 39 | 480 | 386 | 0.804 | 1.88E-04 | 1147 |
| 40 | 262 | 129 | 0.492 | 6.10E-04 | 4447 |
| 41 | 68 | 36 | 0.529 | 5.47E-04 | 864 |
| 42 | 266 | 219 | 0.623 | 1.67E-04 | 579 |
| 43 | 1473 | 1117 | 0.758 | 2.39E-04 | 4462 |
| 44 | 87 | 41 | 0.471 | 6.47E-04 | 1759 |
| 45 | 120 | 58 | 0.483 | 6.26E-04 | 2193 |
| 46 | 96 | 65 | 0.663 | 3.53E-04 | 506 |
| 47 | 223 | 186 | 0.834 | 1.56E-04 | 460 |
| 48 | 208 | 108 | 0.519 | 5.64E-04 | 2855 |
| 49 | 234 | 119 | 0.509 | 5.82E-04 | 3490 |
| 50 | 835 | 725 | 0.866 | 1.22E-04 | 1468 |

The first temperature ($T_1$) and the second temperature ($T_2$) are not limited to the foregoing temperatures.

Description will be directed below to an example showing how to measure the depth and a relative dimensional factor of a defect.

In this experiment, TEM observed depths and scattered beam intensities were measured with respect to two defect samples for the comparison of defect sizes. Actually, the measurement of TEM observed depth $d_{TEM}$ may be made once for a reference defect, and on the basis of the result obtained there may be calculated a defect depth, d, and a relative dimensional factor, A, of a defect in each object to be measured.

Sample ① (TEM observed depth $d_{TEM} = 7.1$ µm)

$I_{RT}$ and $I_{70}$ were found to be 350 and 185, respectively, (RT=23° C., 70=70° C.), so from equation (7):

$$\Delta\alpha = (-1/2d) \cdot \ln(I_T/I_{RT}) \quad (19)$$

Thus, $\Delta\alpha = 448.998$ (cm$^{-1}$)

Sample ② (TEM observed depth=5.3 µm)

$I_{RT}$ and $I_{70}$ were found to be 443 and 279, respectively, so from equation (19), $\Delta\alpha=436.186$ (cm$^{-1}$).

A mean value of $\Delta\alpha$ (sample ①)=448.998 (cm$^{-1}$) and $\Delta\alpha$ (sample ②)=436.186 (cm$^{-1}$) is calculated to be 442.592 (cm$^{-1}$).

Using this mean value of $\Delta\alpha$ as $\Delta\alpha$, the depth d (a measured scattered beam depth d) was determined from a set ($I_{RT}$, $I_{70}$) of measured scattered beam intensities and in accordance with equation (19) with respect to each of samples ① and ②. The results obtained, which are shown in table below, correspond with TEM observed depths.

| Sample | TEM Observed Depth $d_{TEM}$ | TEM Observed Volume V | Measured Scattered Beam Depth d | Dimensional Factor A |
|---|---|---|---|---|
| Sample ① | 7.1 μm | 0.0076 μm³ | 7.2 μm | 9463 |
| Sample ② | 5.3 μm | 0.0038 μm³ | 5.2 μm | 5192 |

Next, a relative dimensional factor A is calculated using $d_{TEM}$. From equation (8):

$$A = I_{RT}/e^{-2\alpha RTd} \quad (20)$$

With respect to sample ①, $\alpha_{RT}=2322$ cm$^{-1}$, $I_{RT}=350$, and $d_{TEM}=7.1$ μm=$7.1\times10^{-4}$ cm are substituted into equation (20) to obtain A=9463.

Likewise, with respect to sample ②, $\alpha_{RT}=2322$ cm$^{-1}$, $I_{RT}=443$, and $d_{TEM}=5.3$ μm=$5.3\times10^{-4}$ cm are substituted into equation (20) to obtain A=192.

Assuming that A is proportional to V² (V stands for a defect volume), an estimated volume ratio V②/V① calculated from TEM observed depths is (A②/A①)$^{0.5}$=(5192/9643)$^{0.5}$=0.741.

Reference will be made below to an example of introducing the relative dimensional factor A using the measured scattered beam depth d and under the same way of thinking as above.

With respect to sample ①, A=9913 is obtained from $\alpha_{RT}=2322$ cm$^{-1}$, $I_{RT}=350$, and d=7.2 μm and in accordance with equation (20).

With respect to sample ②, A=4956 is obtained from $\alpha_{RT}=2322$ cm$^{-1}$, $I_{RT}=443$, and d=5.2 μm and in accordance with equation (20).

An estimated volume ratio V②/V① calculated from measured scattered beam depths is (A②/A①)$^{0.5}$=(4956/9913)$^{0.5}$=0.707.

Further, the relative dimensional factor A can be obtained directly from the intensity of scattered beam.

With respect to sample ①, $\alpha_{RT}=2322$ cm$^{-1}$, $\alpha_T=\alpha_{RT}+\Delta\alpha=2764$ cm$^{-1}$, $I_{RT}=350$, and $I_T=185$ are substituted into equation (10) to obtain A=9925.

With respect to sample ②, $\alpha_{RT}=2322$ cm$^{-1}$, $\alpha_T=\alpha_{RT}+\Delta\alpha=2764$ cm$^{-1}$, $I_{RT}=443$, and $I_T=279$ are substituted into equation (10) to obtain A=5010.

An estimated volume ratio V②/V① calculated from scattered beam intensities is (A②/A①)$^{0.5}$=(5010/9925)$^{0.5}$=0.710.

On the other hand, since the TEM observed volume ratio V②/V① (TEM) is equal to 0.5, it is seen that a rough comparison of defect sizes can be made using A no matter which of the measured defect depth $d_{TEM}$ and the measured scattered beam depth d may be used.

The defect volume ratio is 0.5× in actual measurement, while it is about 0.7× in the embodiment of the present invention, with a slight difference being recognized between the two. But even with this order of accuracy, it is possible to effect comparison to a satisfactory extent because it has heretofore been impossible to even check which of two defects is the larger.

According to the present invention, it is possible to measure any type of wafer.

EXAMPLE 3

Measuring the Number of Crystal Defects

Using the apparatus shown in FIG. 1, a laser beam (about 1.8 eV) having a wavelength of 680 nm was applied to a polished specular surface of Si wafer (Si band gap: 1.12 eV) at an angle near Brewster angle (73.7°) and the intensity of a scattered beam from a defect present in a wafer subsurface layer of a depth corresponding approximately to the penetration depth of the laser beam was measured.

Figure 5:
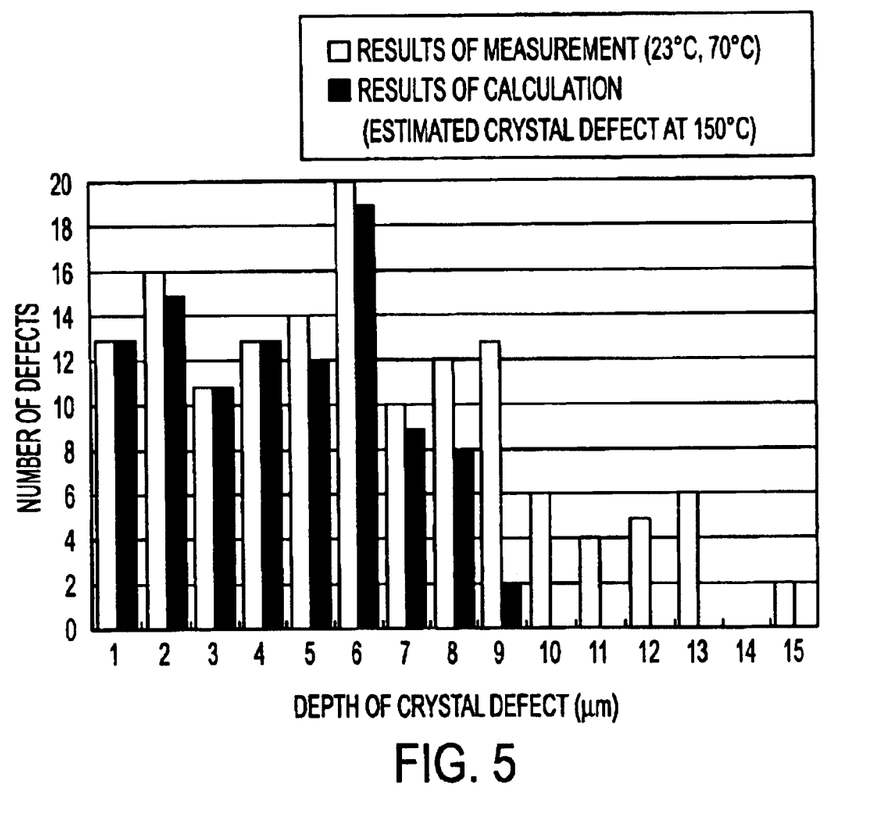
FIG. 5 is a diagram comparing the results of having measured defects present in a subsurface layer of a semiconductor waver at two temperatures and estimated measurement results for the same defect at another temperature which are estimated from the former results.

With reference to FIG. 5, a description will now be given of an experiment in which a change in the distribution of detected defects caused by a change in temperature was predicted. This prediction is for explaining the principle of the present invention in an easily understandable manner.

FIG. 5 shows in a comparative manner the distribution (indicated in white) of defects in crystal detected by a single wavelength, two-temperature type, laser scattering tomography of Si wafer at 23° C. and 70° C. and the distribution (indicated in black) of defects estimated by calculation from the results obtained and at a temperature (150° C.) different from the said two temperatures.

In accordance with the aforementioned tomography there was made measurement actually at two different temperatures of 23° C. and 70° C., and on the basis of the measured values it was predicted how the distribution in the depth direction of defects would change at a measurement temperature of 150° C. for example. In this prediction there was used the absorption coefficient obtained by equation (11). The results obtained are as shown in Tables 5 to 7 and FIG. 5.

The results obtained at 150° C. in FIG. 5 are based on the calculation in which the lower limit of a measurable scattered beam intensity is set at 22, with lower intensity data being excluded. Although the upper limit of depth shown in FIG. 5 is 15 μm, actual data include depths exceeding 20 μm.

TABLE 5

| Scattered beam intensity at 70° C. | Depth, d (μm) | Value A reflecting crystal defect size | Estimated scattered beam intensity at 150° C. |
|---|---|---|---|
| 118 | 4.6 | 1493 | 37 |
| 406 | 6.0 | 10579 | 92 |
| 2533.3 | 1.0 | 4269 | 1998 |
| 108 | 12.9 | 126592 | 4 |
| 123 | 6.0 | 3375 | 27 |
| 34 | 15.3 | 150550 | 1 |
| 136 | 5.8 | 3232 | 32 |
| 282 | 7.3 | 15747 | 45 |
| 205 | 6.8 | 8417 | 38 |
| 49 | 14.9 | 174059 | 1 |
| 38 | 11.1 | 16300 | 2 |
| 250 | 4.1 | 2310 | 91 |
| 108 | 8.1 | 9148 | 14 |
| 496 | 3.8 | 3965 | 193 |
| 536 | 7.6 | 34017 | 81 |
| 34 | 14.9 | 117061 | 1 |
| 163 | 8.2 | 14712 | 21 |
| 200 | 8.4 | 20254 | 24 |
| 125 | 6.7 | 4776 | 24 |

TABLE 5-continued

| Scattered beam intensity at 70° C. | Depth, d (μm) | Value A reflecting crystal defect size | Estimated scattered beam intensity at 150° C. |
|---|---|---|---|
| 139 | 9.5 | 25905 | 13 |
| 946.11 | 2.4 | 3439 | 526 |
| 713 | 3.7 | 5491 | 282 |
| 22 | 4.5 | 264 | 7 |
| 201 | 5.0 | 3026 | 59 |
| 346 | 5.5 | 6924 | 89 |
| 346 | 6.7 | 13356 | 66 |
| 88 | 8.6 | 10046 | 10 |
| 313 | 0.9 | 514 | 250 |
| 623 | 5.1 | 10361 | 173 |
| 34 | 8.5 | 3668 | 4 |
| 580 | 0.2 | 665 | 545 |
| 1095 | 0.1 | 1146 | 1073 |
| 199 | 4.8 | 2732 | 60 |
| 536 | 4.4 | 5889 | 180 |
| 78 | 8.7 | 8939 | 9 |
| 243 | 5.0 | 3840 | 69 |
| 620 | 2.1 | 1964 | 367 |
| 100 | 4.7 | 1319 | 31 |
| 946.11 | 1.9 | 2742 | 583 |
| 30 | 8.3 | 2861 | 4 |
| 56 | 4.3 | 581 | 19 |
| 526 | 2.5 | 2040 | 284 |
| 795 | 3.4 | 5195 | 338 |
| 44 | 6.4 | 1437 | 9 |
| 163 | 5.3 | 3052 | 43 |
| 39 | 1.4 | 85 | 27 |
| 280 | 7.9 | 20980 | 39 |
| 506 | 2.3 | 1803 | 284 |
| 37 | 15.9 | 227897 | 1 |
| 1788.82 | 4.7 | 23014 | 560 |
| 176 | 7.4 | 9872 | 28 |
| 256 | 5.6 | 5562 | 63 |
| 30 | 7.5 | 1794 | 5 |
| 91 | 9.7 | 18748 | 8 |
| 1035 | 0.3 | 1206 | 965 |
| 268 | 8.5 | 28519 | 32 |
| 576 | 4.1 | 5304 | 210 |
| 205 | 7.7 | 13560 | 30 |
| 310 | −0.2 | 279 | 325 |
| 46 | 11.9 | 31620 | 2 |
| 356 | 3.6 | 2585 | 144 |
| 21 | 16.7 | 201851 | 0 |

TABLE 6

| Scattered beam intensity at 70° C. | Depth, d (μm) | Value A reflecting crystal defect size | Estimated scattered beam intensity at 150° C. |
|---|---|---|---|
| 523 | 1.9 | 1489 | 325 |
| 533 | 2.2 | 1789 | 307 |
| 453 | 4.1 | 4301 | 163 |
| 106 | 7.6 | 6732 | 16 |
| 147 | 4.0 | 1301 | 55 |
| 76 | 11.0 | 31022 | 5 |
| 500 | 3.3 | 3024 | 220 |
| 195 | 1.1 | 353 | 149 |
| 180 | 1.5 | 402 | 125 |
| 626 | 3.5 | 4244 | 262 |
| 630 | 1.5 | 1465 | 429 |
| 73 | 8.3 | 6975 | 9 |
| 39 | 9.9 | 9057 | 3 |
| 376 | 7.8 | 27628 | 53 |
| 141 | 11.2 | 66265 | 9 |
| 134 | 5.2 | 2290 | 37 |
| 626 | 2.2 | 2144 | 358 |
| 1065 | 0.1 | 1151 | 1028 |
| 136 | 6.3 | 4303 | 28 |
| 26 | 1.6 | 62 | 17 |
| 57 | 16.3 | 433888 | 1 |
| 336 | 3.4 | 2124 | 145 |

TABLE 6-continued

| Scattered beam intensity at 70° C. | Depth, d (μm) | Value A reflecting crystal defect size | Estimated scattered beam intensity at 150° C. |
|---|---|---|---|
| 21 | 15.8 | 122344 | 0 |
| 1085 | −1.3 | 512 | 1486 |
| 406 | 5.5 | 8100 | 104 |
| 175 | 8.8 | 21442 | 20 |
| 646 | 2.6 | 2636 | 341 |
| 1030 | −0.5 | 799 | 1156 |
| 32 | 15.8 | 179035 | 1 |
| 29 | 22.7 | 7289423 | 0 |
| 164 | 0.4 | 199 | 150 |
| 95 | 5.8 | 2245 | 23 |
| 127 | 6.2 | 3779 | 27 |
| 25 | 15.7 | 133336 | 1 |
| 163 | 9.9 | 36172 | 14 |
| 41 | 11.3 | 20346 | 2 |
| 29 | 12.9 | 33670 | 1 |
| 1819.84 | 5.3 | 33284 | 485 |
| 211 | 3.7 | 1566 | 85 |
| 216 | 4.7 | 2843 | 67 |
| 28 | 17.5 | 418963 | 0 |
| 283 | 1.3 | 587 | 203 |
| 216 | 1.4 | 470 | 152 |
| 170 | 5.9 | 4372 | 39 |
| 167 | 9.6 | 32081 | 15 |
| 122 | 8.0 | 9812 | 17 |
| 77 | 10.8 | 25610 | 5 |
| 200 | 5.7 | 4619 | 48 |
| 296 | 3.9 | 2481 | 113 |
| 53 | 12.3 | 44917 | 2 |
| 706 | 5.8 | 16957 | 166 |
| 705 | 4.7 | 9079 | 220 |
| 65 | 9.8 | 13884 | 6 |
| 308 | 4.2 | 3044 | 109 |
| 306 | 6.9 | 13282 | 55 |
| 255 | 1.3 | 524 | 184 |
| 680 | 1.2 | 1338 | 500 |
| 895 | 1.0 | 1523 | 703 |
| 340 | 1.5 | 761 | 236 |
| 31 | 7.3 | 1671 | 5 |
| 132 | 8.6 | 14817 | 15 |
| 800 | 2.8 | 3743 | 396 |
| 194 | 7.1 | 9653 | 33 |

TABLE 7

| Scattered beam intensity at 70° C. | Depth d (μm) | Value A reflecting crystal defect size | Estimated scattered beam intensity at 150° C. |
|---|---|---|---|
| 360 | 5.5 | 7502 | 90 |
| 570 | 2.6 | 2342 | 300 |
| 157 | 6.6 | 5915 | 30 |
| 65 | 5.4 | 1247 | 17 |
| 433 | 5.7 | 9896 | 104 |
| 271 | 1.7 | 698 | 176 |
| 41 | 12.9 | 47735 | 2 |
| 24 | 12.6 | 24474 | 1 |
| 353 | 7.5 | 21592 | 54 |
| 430 | 0.7 | 619 | 364 |
| 330 | 5.9 | 8216 | 76 |
| 693 | 4.0 | 6140 | 257 |
| 61 | 4.0 | 535 | 23 |
| 39 | −5.9 | 2 | 171 |
| 39 | 11.7 | 24080 | 2 |
| 660 | 5.9 | 16299 | 153 |
| 820 | 3.9 | 6908 | 311 |
| 42 | 12.4 | 37169 | 2 |
| 116 | 8.9 | 15068 | 13 |
| 161 | 1.3 | 329 | 116 |
| 543 | 6.0 | 14738 | 121 |
| 44 | 10.8 | 16175 | 3 |
| 32 | 10.8 | 11892 | 2 |
| 37 | 15.2 | 157015 | 1 |

TABLE 7-continued

| Scattered beam intensity at 70° C. | Depth d (μm) | Value A reflecting crystal defect size | Estimated scattered beam intensity at 150° C. |
|---|---|---|---|
| 99 | 1.5 | 230 | 67 |
| 22 | 17.1 | 261469 | 0 |
| 456 | 2.0 | 1367 | 277 |
| 201 | 5.5 | 4111 | 51 |
| 80 | 7.2 | 4153 | 13 |
| 955 | 2.1 | 3072 | 561 |
| 663 | 1.7 | 1687 | 434 |

Although in Tables 5 to 7 there are described only measured values of scattered beam intensities at 70° C., actually scattered beam intensities at 23° C. have also been measured. On the basis of these measured values of scattered beam intensities at 70° C. and 23° C. there were obtained the depth (d) of each defect and the value (A) reflecting the size of the defect in accordance with the foregoing equations (16) and (12). The "estimated scattered beam intensity at 150° C." in Tables 5 to 7 is calculated on the basis of "measured value of scattered beam intensity at 70° C." and "depth d" and in accordance with the following equation (21).

With reference to equation (16), when scattered beam measurement temperatures are 70° C. and 150° C., the depth d is:

$$d = \ln(I_{150}/I_{70})/-2(\alpha_{150}-\alpha_{70})$$

Scattered beam intensity $I_{150}$ is given as:

$$I_{150} = I_{70}\exp\{-2(\alpha_{150}-\alpha_{70})d\} \quad (21)$$

In Tables 5 to 7, even crystal defects at deeper positions than 15 μm are measured at 70° C.

FIG. 5 has been prepared on the basis of such Tables 5 to 7.

A description will now be given about how to derive measurement results (white) in FIG. 5. First, the values of depth d shown in Tables 5 to 7 were rearranged in order of size and classified 1 μm by 1 μm, for which the number of depths was calculated as the number of defects (white). How to classify the depth will now be described. For example, in Tables 5 to 7, the number of defects present in the range of 4.0 μm excl. to 5.0 um incl. is shown at the column of depth 5 μm in FIG. 5. As to depths d exceeding 15 μm, they are omitted.

The following description is now provided about how to derive measurement results (black) in FIG. 5. First, scattered beam intensities estimated at 150° C. were calculated on the basis of the measurement results of scattered beam intensities at 70° C. and in accordance with equation (21). The results obtained are shown in the rightmost-end columns of Tables 5 to 7. Then, only the scattered beam intensities not lower than 22 at 150° C. were picked out. For the scattered beam intensities thus picked out, the number of defects (black) was derived by the same method as the method adopted for deriving the number of defects (white). Reference to FIG. 5 shows that defects up to the depth of 10 μm can be predicted at 150° C.

Thus, it turns out that by changing the wafer temperature there is obtained a distribution of defects present depth by depth and up to an arbitrary depth. By adding all of the measured scattered beams it is possible to determine the total number of defects present up to an arbitrary depth.

Figure 6:
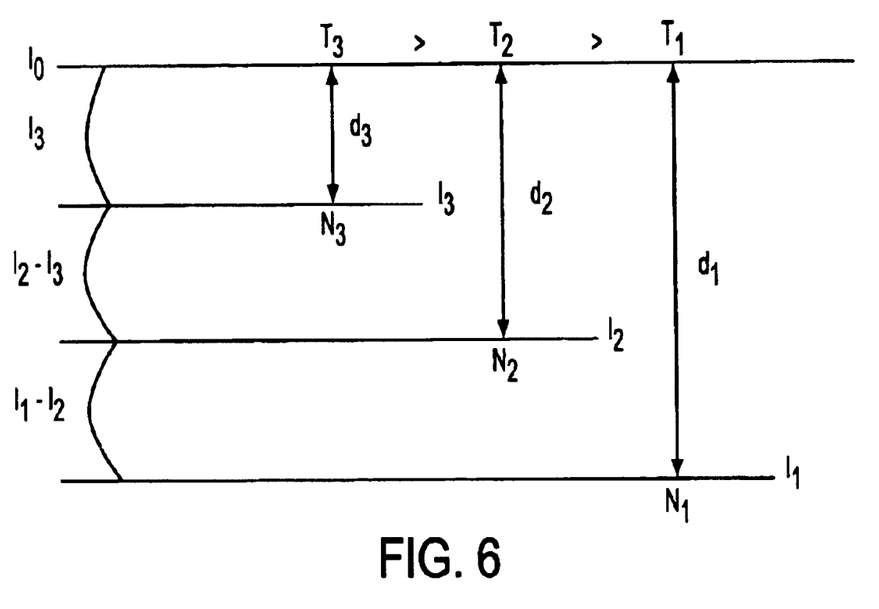
FIG. 6 is a diagram explaining the measurement principle of the present invention with use of a schematic diagram of a wafer section.

FIG. 6 is a schematic diagram of a wafer section which is for explaining how the depth of defect and temperature are related to each other. In the same figure, $T_1$ is temperature, $d_1$ is the depth of a defect present at a measurable deepest position, $l_1$ is a wafer layer from a wafer surface $l_0$ down to a depth of $d_1$, and $N_1$ is the number of defects present in the layer $l_1$. Regarding the temperatures $T_1$, $T_2$, and $T_3$ in the same figure, it is here assumed that there exists the relationship of $T_1<T_2<T_3$.

For example, at a low temperature ($T_1$), a laser beam penetrates to a deep position in the wafer, while at a high temperature ($T_3$), the laser beam penetrates to a shallow position. That is, if the temperature is low ($T_1$), there are measured scattered beams generated from defects present in deep positions up to ($d_1$), while if the temperature is high ($T_3$), there are measured defects present in shallow positions up to ($d_3$). Thus, the number of scattered beams measured at a certain temperature corresponds to the number of defects present in positions up to a predetermined depth proportional to the said temperature. In the present invention, which is based on this principle, scattered beams in a wafer are measured at different temperatures to determine the number of defects present up to a desired depth of the wafer.

For example, moreover, it is seen that if the numbers of defects, $N_1$ and $N_2$, in layers $l_1$ and $l_2$ from the wafer surface at temperature $T_1$ and a higher temperature $T_2$ are measured and the difference between the two is obtained, it is possible to determine the number of defects, ($N_1-N_2$), present in a layer ($l_1-l_2$) which results from exclusion of the layer $l_2$ from the layer $l_1$.

Although the measurement temperatures used in the above experiments are 23° C., 70° C., and 150° C., no limitation is made thereto.

According to the present invention, the depth of each individual defect can be measured in a non-destructive manner. Even a defect depth of about 10 μm can be measured.

The wafer defect measuring method and apparatus according to the present invention do not require the use of any complicated structure of an optical system, which is advantageous in point of detection sensitivity and cost. Particularly, even without using plural laser beam sources it is possible to measure in a non-destructive manner the depth from the wafer surface of each defect present in a subsurface layer of a semiconductor wafer. Also as to information on the actual size (dimension) of a defect, it is possible to obtain such information in a non-destructive manner and also possible to compare actual sizes (dimensions) of defects.

According to the present invention, the sizes (dimensions) of any two crystal defects can be compared with each other in a non-destructive manner.

Further, according to the present invention, the number of defects up to an arbitrary depth in a wafer surface layer can be calculated in a non-destructive manner. Particularly, by changing the wafer temperature, the number of defects present in each layer can be calculated while changing the penetration depth of laser beam substantially continuously for each predetermined layer (e.g., at every 2 μm from the wafer surface).

When the measurement is made at any one temperature, it is possible to detect the number of defects at high speed.

What is claimed is:

1. A method for measuring defects present in a surface layer of a wafer having a wafer surface in a non-destructive manner, comprising:
  measuring intensities of scattered beams at two or more temperatures of the wafer,
  correcting the measured intensities of the scattered beams by using an absorption coefficient of silicon, and measuring depths of defects from the wafer surface on the basis of the measured intensities of the scattered beams;

wherein the scattered beams originate from a single laser beam;

wherein the wafer temperature is controlled by means of a temperature controller;

wherein the wafer is heated by a heater, and the temperature of the wafer is changed by changing the temperature of the heater; and wherein the single laser beam which has a larger energy than a band gap of silicon, is applied to the wafer surface obliquely.

2. The method of claim 1 wherein the wafer is a silicon wafer.

3. The method of claim 1, wherein the single laser beam has a single wavelength.

4. A wafer defect measuring method comprising:

radiating a laser beam having a larger energy than the band gap of silicon obliquely to a surface of a silicon wafer held at a first temperature ($T_1$), detecting the intensity of a scattered laser beam from a defect present near the wafer surface, radiating the laser beam obliquely to the wafer surface held at a second temperature ($T_2$) different from the first temperature ($T_1$), detecting the intensity of a scattered laser beam from the defect present near the wafer surface, and correcting measured intensities of the scattered laser beams by using an absorption coefficient of silicon on the basis of the difference between the two scattered laser beam intensities at the first temperature ($T_1$) and the second temperature ($T_2$) so as to calculate the depth of the defect from the wafer surface.

5. The method of claim 4, wherein the laser beam has a single wavelength.

6. A wafer defect measuring method comprising radiating a laser beam having a larger energy than the band gap of silicon obliquely to a surface of a wafer held at a first temperature ($T_1$), detecting the intensity of a scattered laser beam from a defect present near the wafer surface, radiating the laser beam obliquely to the wafer surface held at a second temperature ($T_2$) different from the first temperature ($T_1$), detecting the intensity of a scattered laser beam from a defect present near the wafer surface, and determining a relative dimensional factor of a defect present in a subsurface layer of the wafer on the basis of the difference between the two scattered laser beam intensities at the first temperature ($T_1$) and the second temperature ($T_2$).

7. The method of claim 6, wherein a plurality of relative dimensional factors are obtained to compare sizes of defects.

8. The method of claim 6, wherein the scattered laser beams are produced by scattering a single laser beam which has a single wavelength.

9. A method for measuring a defect present in a subsurface layer of an object to be measured in a non-destructive manner, wherein depths of crystal defects from a surface of the object to be measured are measured by detecting the intensities of scattered laser beams at two or more temperatures of the object and thereafter a relative dimensional factor is determined.

10. The method of claim 9, wherein sizes of two or more defects are compared with each other.

11. The method of claim 9, wherein the scattered laser beams are produced by scattering a single laser beam which has a single wavelength.

12. A wafer defect measuring apparatus comprising:

a wafer rest on which a silicon wafer is disposed, a laser which produces a laser beam having a larger energy than the band gap of silicon is radiated to a surface of the wafer obliquely, and a scattered laser beam from a defect present near the wafer surface is detected, wherein the wafer rest is provided with a temperature controller for the wafer, the intensities of scattered laser beams at two or more temperatures of the wafer are detected, and a relative dimensional factor is determined on the basis of the detected scattered laser beam intensities.

13. The method of claim 12, wherein the scattered laser beams are produced by scattering a single laser beam which has a single wavelength.

14. A wafer defect measuring method comprising scanning a laser beam over a surface of a wafer and measuring a defect present in a subsurface layer of the wafer in a non-destructive manner, wherein any one of plural temperatures of the wafer is selected, and the intensity of a scattered laser beam in the wafer up to a penetration depth of the laser beam at the selected temperature is measured to determine the number of defects at a desired depth of the wafer subsurface layer, wherein the number of defects in a first layer and the number of defects in a second layer from the wafer surface at a first temperature ($T_1$) and a second temperature ($T_1$) higher than the first temperature are measured and the difference between the two numbers is calculated to determine the number of defects present in a third layer which results from exclusion of the second layer from the first layer.

15. The method of claim 14, wherein the intensities of scattered laser beams at two or more selected temperatures are measured to determine the number of defects at the desired depth of the wafer subsurface layer.

16. The method of claim 14, wherein the laser beam has a larger energy than the band gap of silicon and the laser beam is radiated obliquely to the surface of the wafer.

17. The method of claim 14, wherein the temperature of the wafer is controlled by a temperature controller, two or more wafer temperatures are selected, and the intensities of scattered laser beams at the selected two or more temperatures are measured to determine the number of defects at the desired depth of the wafer subsurface layer.

18. The method of claim 17, wherein the wafer is heated with a heater and the wafer temperature is changed to two or more temperatures by changing the temperature of the heater.

19. A method for measuring a defect present in a subsurface layer of a wafer in a non-destructive manner, wherein a relative dimensional factor of a defect present in the wafer subsurface layer is determined by detecting the intensities of scattered beams at two or more temperatures of the wafer, and wherein the scattered beams are produced by scattering a single laser beam which has a single wavelength.

* * * * *